United States Patent [19]

Hopkins et al.

[11] Patent Number: 4,767,994
[45] Date of Patent: Aug. 30, 1988

[54] MULTI-PURPOSE VOLTAMETRIC ANALYZER

[75] Inventors: Thomas R. Hopkins; James F. Stewart, both of Bartlesville, Okla.

[73] Assignee: Phillips Petroleum Company, Bartlesville, Okla.

[21] Appl. No.: 905,435

[22] Filed: Sep. 10, 1986

[51] Int. Cl.⁴ ........................................... G01N 27/46
[52] U.S. Cl. .................................... 324/438; 324/439; 204/406
[58] Field of Search ...................... 204/403, 406, 415; 324/438, 439

[56] References Cited

U.S. PATENT DOCUMENTS

| | | | |
|---|---|---|---|
| 3,539,455 | 11/1970 | Clark, Jr. et al. | 204/1 |
| 4,073,713 | 2/1978 | Newman | 204/195 B |
| 4,207,146 | 6/1980 | Kunte | 204/406 |
| 4,394,222 | 7/1983 | Rohr | 204/406 |
| 4,460,967 | 7/1984 | Krull et al. | 364/497 |
| 4,502,937 | 3/1985 | Yagi | 324/438 |
| 4,556,635 | 12/1985 | Hitzman et al. | 435/25 |
| 4,655,880 | 4/1987 | Liu | 204/1 T |

OTHER PUBLICATIONS

Hopkins, "A multipurpose Enzyme Sensor Based on Alcohol Oxidase", American Brotechnology Laboratory, Sep./Oct. 1985.

Primary Examiner—G. P. Tolin
Assistant Examiner—Jeffrey A. Gaffin
Attorney, Agent, or Firm—George E. Bogatie

[57] ABSTRACT

An instrument for measuring the concentration of a wide variety of important chemical and biochemical substances is provided which comprises an enzyme based voltametric sensor, and electronic circuitry for conditioning an output signal from the sensor. The instrument includes one or more aqueous oxidase enzymes mechanically coupled to a polarographic cell oxygen detector wherein the concentration of a substance is inferred from measurement of the depletion of oxygen resulting from an oxidation reaction catalyzed by the oxidase enzyme. The electronic circuitry includes current to voltage conversion, nulling an unneeded base current signal, and temperature compensation.

9 Claims, 2 Drawing Sheets

MULTI-PURPOSE VOLTAMETRIC ANALYZER

The present invention relates to apparatus and method for the accurate measurement of the concentration of a substance. In one aspect it relates to electronic circuitry, associated with a polarographic cell oxygen detector, to condition a current signal for measurement and recording.

The use of voltametric techniques, such as amperometry and polarography have become popular, especially in the medical and biological fields, for measurement of various substances. In addition enzymes have been used in conjunction with polarographic cells to extend the measurement potential to substances that are not polarographically active. This extension is accomplished where the unknown substance to be measured is not polarographically active, but a material consumed by an enzymatic reaction with that unknown substance is detectable. For example, it is known that ethanol is not polarographically active but that the following reaction takes place in presence of the enzyme alcohol oxidase:

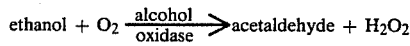

$$\text{ethanol} + O_2 \xrightarrow[\text{oxidase}]{\text{alcohol}} \text{acetaldehyde} + H_2O_2$$

This reaction and numerous other enzymatic reactions which are characterized by the uptake of $O_2$ are significant in facilitating chemical analysis measurements in complex samples because of the remarkable sepcificity of enzymes and the ability of the enzyme to catalyze reactions under mild conditions. Equally important, however, in this reaction is that a polarograhic or galvanometric cell oxygen detector responds in a linear manner to the concentration of the nonpolarograhpic substance. The linear relation between $O_2$ uptake and the concentration of the nonpolarographic substance simplifies processing of the signal from the oxygen detector as well as simplifying calibration procedures for analysis of complex samples.

Accordingly it is an object of this invention to provide a multi-purpose enzyme sensor having the capacity to analyze compounds which may be enzymatically correlated to a polarographically active material or compounds which are the substrates of a known oxidase enzyme. Another object of the present invention is to provide an electronic circuit optimized for conditioning a current signal from an oxygen detector.

In accordance with the present invention apparatus and method are provided for accurately and rapidly measuring the concentration of a wide variety of important chemical and biochemical substances. The apparatus includes an enzyme sensor and associated electronic circuits to measure the signal from the enzyme sensor.

The enzyme sensor employed in the practice of the present invention comprises a probe type oxygen detector which provides an output current representative of the concentration of oxygen in contact with a sensitive area located on the tip of the probe. The probe is used in conjunction with an appropriate oxidase enzyme or combination of enzymes by covering the probe tip with a thin layer of an aqueous oxidase enzyme. For example the oxidase enzyme can be contained in a gel that is applied to the probe tip with a spatula. The thickness of the oxidase enzyme layer affects the response time for a measurement e.g. a relatively thick layer reduces the time required for the instrument response to reach its final value, however, the thick layer also increases the time required for the output signal to return to its base value. In the embodiment illustrated by FIG. 3, the preferred thickness of the oxidase enzyme layer results in a response that reaches its final value in about four minutes. Contact of the probe tip with the thin layer of aqueous oxidase enzyme produces a base current from the oxygen detector.

Thereafter, contacting the oxidase enzyme layer with a solution of the substance to be measured catalyzes a reaction of the substance with oxygen in the oxidase enzyme layer, and wherein this reaction consumes oxygen from the aqueous oxidase enzyme layer. The consumption of oxygen in the aqueous oxidase enzyme layer reduces the concentration of the dissolved oxygen contacting the sensitive area on the probe tip and correspondingly reduces the magnitude of the output current signal from the oxygen detector. Therefore, from an initial base value, the output current of the oxygen detector is reduced in direct proportion to the concentration of the substance contacting the oxidase enzyme layer.

Additional apparatus employed in the practice of the present invention includes electronic circuitry for conditioning the current signal generated by the oxygen detector. The conditioning equipment includes an operational amplifier used to convert a current signal from the oxygen detector to a proportional voltage signal. A variable resistor, external to the operational amplifier, is provided to adjust the voltage signal to an appropriate level for measuring and recording on a strip chart recorder. Further the operational amplifier is provided with an external potentiometer for "nulling" the base value signal that is generated by the probe in the absence of a reaction which depletes oxygen in the thin oxidase enzyme layer. For example, the base current can be generated with the oxidase enzyme layer exposed to a buffer solution. This nulling step greatly increases the sensitivity of the measurement since only the change in current from base value is converted to a proportional voltage. Therefore, by using the variable resistor to adjust voltage level, the change in current can be resolved over the full scale of the strip chart recorder.

Also included are circuits for supplying a constant polarizing voltage to the oxygen detector, and a circuit utilizing a thermistor for temperature compensation. It is noted that the temperature compensation employed provides a logarithmic correction between the output voltage and temperature of the oxygen detectors.

Other objects of advantages of the invention will be apparent from the foregoing description of the invention and the appended claims as well as from the detailed description of the drawings in which:

Figure 1:
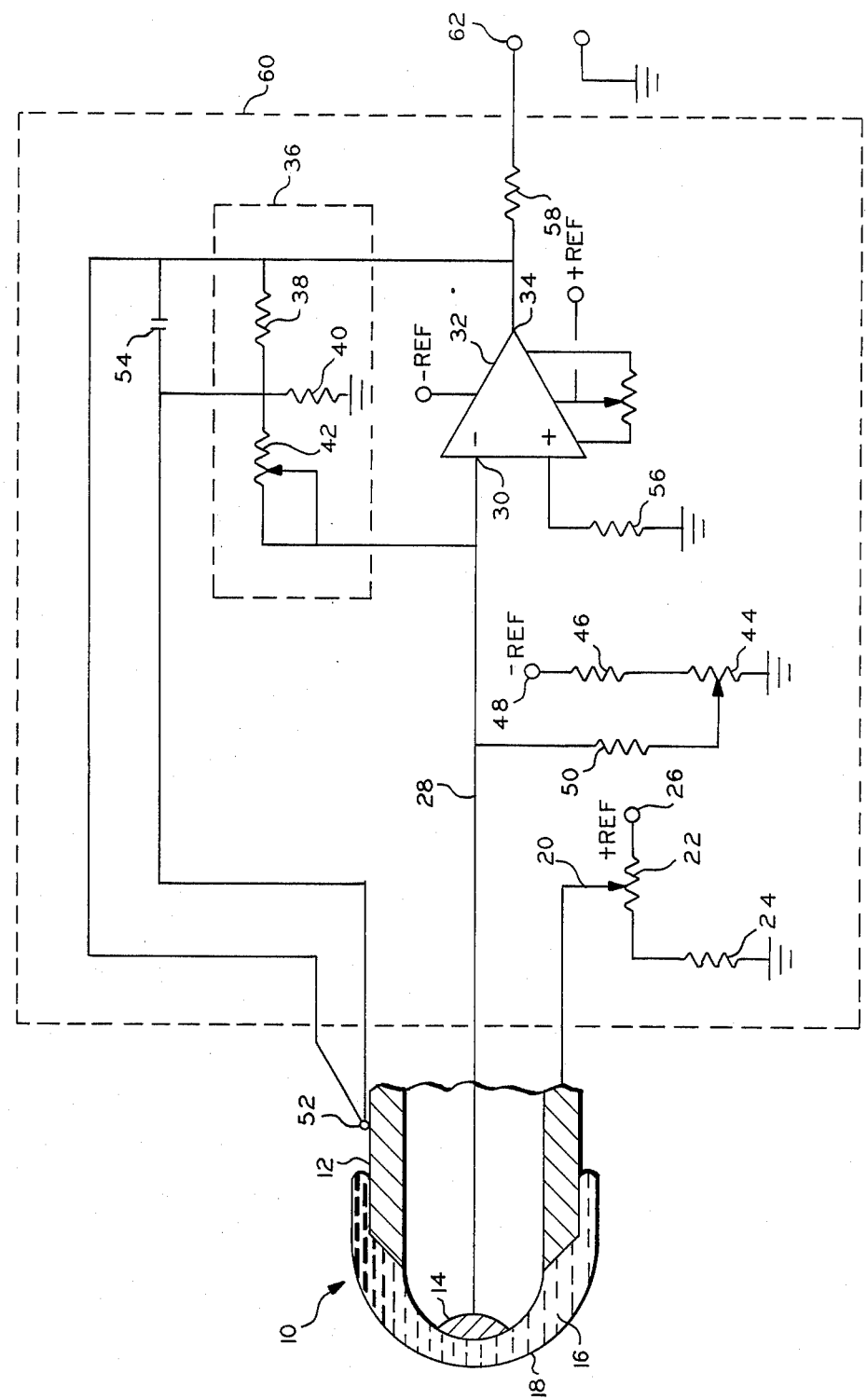
FIG. 1 is a schematic diagram showing the signal conditioning circuitry of the present invention connected to a probe type polarographic cell oxygen detector.

The invention is described in terms of use of an alcohol oxidase enzyme layer coupled to the sensitive area of an oxygen electrode. However, the present invention is not limited to a single enzyme layer since it would be obvious to a person skilled in the chemical art that combinations of specific oxidase enzymes can be used to extend the utility of the present invention. For example ascorbic acid oxidase, 1-amino acid oxidase, d-amino acid oxidase, galactoxidase, xanthine oxidase and uric acid oxidase are all useful catalysts. Table I is a partial list of substances subject to analysis by the present invention. This table includes compounds which have actually been measured using an oxidase/dissolved oxygen probe combination, and compounds which are the substrate of a known oxidase enzyme.

age (usually about 0.8 volts) across the electrodes 12 and 14.

Another electrical conductor 28 connects electrode 14 to the inverting input 30 of operational amplifier 32. Operational amplifier 32 is configured for operation as a current to voltage converter with the proportionality between current and voltage determined by the T network 36 connected between the output 34 and inverting input 30. The operational amplifier 32, therefore, derives its feedback signal from a voltage divider formed by resistors 38 and 40. Variable resistor 42 provides adjustment for the proportionality between voltage and

TABLE I

| | | |
|---|---|---|
| Acetaldehyde | Formaldehyde | Methyl-D-Glucose |
| Acetic Acid | Formic Acid | Methyl-L-Amino Acids |
| Adenoisine 5'-Monophosphate | Fructose | Manoamine |
| Alanine | Furfural | NAD |
| Alcohol Esters | Furfuryl Alcohol | NADH |
| Aliphatic Nitro Compounds | Galactonolactone | Nitroethane |
| Alkaline Phosphatase | Galactose | Octylamine |
| Allyl Alcohol | Glucopyranose | Oxalic Acid |
| Altronolactone | Glucose | Pectin |
| Aminophenols | Glutamate | Pectin Esterase |
| Aromatic Amines | Glutamate Pyruvate Trasaminase | Phenol |
| Ascorbic Acid | Glyceraldehyde | Phenylalanine |
| Aspartate | Glycerin | Phenylenediamine |
| Benzaldehyde | Glyokylate | Polyamines |
| Benzidine | Hydrogen Peroxide | Proline |
| Benzylamine | Hydroquinone | Propanol |
| Butanol | Hydroxymethyl Furfural | Purine |
| Butyric Acid | Hydroxphenylacetic Acid | Putrescin |
| Cadaverin | Hydroxphenyllactic Acid | Pyridoxamine Phosphate |
| Carbohydrates | Hypoxanthine | Pyrocatechol |
| Catechol | Hydroxy Acids | Pyrogallol |
| Chlorogenic Acid | Inorganic Phosphorus | Pyruvic Acid |
| Cholesterol | Isopropanol | Raffinose |
| Choline | Lactase | Sarcosine |
| Cholinesterase | Lactate Dehydrogenase | Sorbose |
| Chymotrypsin | Lactic Acid | Spermidine |
| Cresol | Lactose | Spermine |
| Dextran | Lipase | Stachyose |
| Diamines | Lysine | Starch |
| Dianisidine | Maltose | Sucrose |
| Dihydro-Orotate | Mandalate | Sulfite |
| Dihydroxyacetone | Mannose | Tyramine |
| Dihydroxyphenylalanine | Manonolactone | Uric Acid |
| Dioxy-D-Glucose | Melibiose | Valine |
| Dioxy-Fluro-D-Glucose | Methanol | Verbascose |
| Erythrose | Methionine | Xanthine |
| Ethanol | Methyl Sulfate | Xylopyranose |
| Ethyl Mercaptan | | |

Figure 2:
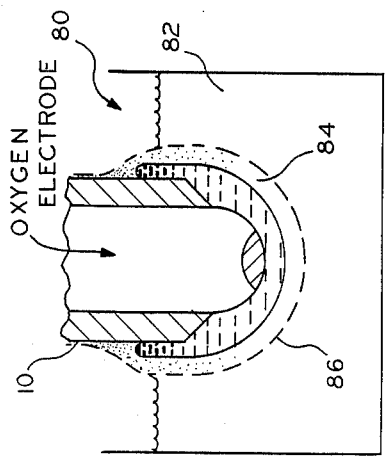
FIG. 2 is a sectional view showing the oxidase enzyme sensor of the present invention.

Also the preferred embodiment illustrated in FIGS. 1 and 2 utilizes a probe type polarographic cell oxygen detector. However the present invention is not limited to this type of detector since other commercially available detectors such as a pH electrode, or ion selective electrode can yield valid measurements.

Referring now to FIG. 1 there is illustrated generally at 10 a probe type polarographic cell oxygen detector connected to a signal conditioning circuit indicated at 60. Detector 10 can be a commercially available probe for example a Beckmann Model 777. The probe 10 has two electrodes 12 and 14 immersed in an electrolyte 16 so that current passes through the electrodes as chemical reactions occur at the surface of an electrode. The electrolyte is contained by membrane 18.

An electrical conductor 20 electrically connects electrode 12 to the moveable contact of potentiometer 22. Potentiometer 22 in combination with fixed resistor 24 forms a voltage divider between a positive reference voltage supplied to terminal 26 and ground. Potentiometer 22 is adjusted to provide a constant polarizing voltcurrent, i.e. output voltage $\approx$[(resistor 42$\times$resistor 38)/resistor 40]$\times$output current. The adjustment knob for variable resistor 42 is therefore located so as to be easily accessible to the user.

Potentiometer 44 in combination with fixed resistor 46 forms a voltage divider between a negative reference voltage supplied between terminal 48 and ground. The moveable contact on potentiometer 44 is connected via fixed resistor 50 to inverting input 30 of operational amplifier 32. This connection of potentiometer 44 provides for nulling an undesired input current by providing a signal equal in magnitude but opposite in polarity to the undesired input signal. The adjustment knob for potentiometer 44 is also located so as to be easily accessible to a user.

Thermistor 52, which is located so as to sense the temperature of the probe 10, can be a commercially available negative coefficient thermistor having any suitable resistance. A preferred resistance is 10K$\Omega$ at 25° C. Thermistor 52 provides temperature compensation required to maintain accuracy over a wide temperature range.

Other circuit components illustrated in signal conditioning circuit 60 include capacitor 54, resistors 56 and 58, and output terminals 62. Capacitor 54 is connected across resistor 38 to reduce high frequency noise, resistor 56 is connected from the non-inverting input of operational amplifier 32 to ground to reduce output offset due to input bias current, and resistor 58 protects the output of operational amplifier 32 against accidental short circuit of output terminal 62.

Commercially available components plus the values of capacitors and resistors which can be utilized in the signal conditioning circuit 60 are as follows:

TABLE II

| COMPONENT | DESCRIPTION |
|---|---|
| Operational Amplifier 32 | Analog Device, AD-OPO7-DN |
| Potentiometer 22 | Newark 12F4414, 250K ohm |
| Potentiometer 42 | Piher PC16-S-7-I-P4-X, 500 ohm log |
| Potentiometer 44 | Newark 81F5748, 5K ohm, 10 turn |
| Resistor 24 | Newark 08F951, 5.11K ohm |
| Resistor 46 | Newark 08F950, 150K ohm |
| Resistor 40 | Newark 08F951, 1.2K ohm |
| Resistor 38 | Newark 08F950, 120K ohm |
| Resistors 50, 56 | Newark 08F951, 100K ohm |
| Resistor 58 | Newark 08F981, 51.1 ohm |
| Capacitor 54 | Newark 15F2113, 0.5 microfarad |

Referring now to FIG. 2 there is illustrated generally at 80 an enzyme sensor which can be immersed in a bulk solution 82. Surrounding the tip of the oxygen detector 10 is an oxidase enzyme layer 84. The oxidase enzyme layer 84 is held next to the tip of probe 10 by a semipermable membrane 86.

In the illustrated embodiment the enzyme layer 84 can be alcohol oxidase. Any alcohol oxidase known in the art or available from commercial supply houses such as Sigma Chemical Co., St. Louis, Mo. may be used.

Alternatively alcohol oxidase can be prepared from an aqueous suspension of *Pichia pastoris*. A detailed description of the preparation of alcohol oxidase from *Pichia pastoris*, as well as suitable methods for holding the alcohol oxidase tightly against the tip of probe 10 is disclosed in Hitzman et al U.S. Pat. No. 4,556,635 which is incorporated herein by reference. For example the oxidase enzyme can be blended with suitable supporting material to form a paste which is held as a thin film on the electrode tip by a membrane permeable (typically hydrated) to the compound whose concentration is to be measured, but impermeable to the enzyme itself. For example the supporting material may be hydrated DEAE Sephadex. For ethanol determinations a suitable membrane is cellulose acetate.

EXAMPLE

To illustrate the operation of the apparatus a first step was preparation of the oxidase enzyme probe. This step required preparation of an oxidase enzyme gel by adding a small amount of buffer to 1.0 mg of dry oxidase enzyme gel. After thorough mixing the gel was thick enough for transfer with a spatula. The thus prepared enzyme gel was applied to the center of a cellulose acetate membrane which had been wetted by presoaking in distilled water. The membrane having the thin layer of oxidase enzyme was placed over the end of the probe, as illustrated in FIG. 2, and a conical cap was pushed over the wet membrane thereby holding the enzyme gel between the membrane and the probe tip.

Figure 4:
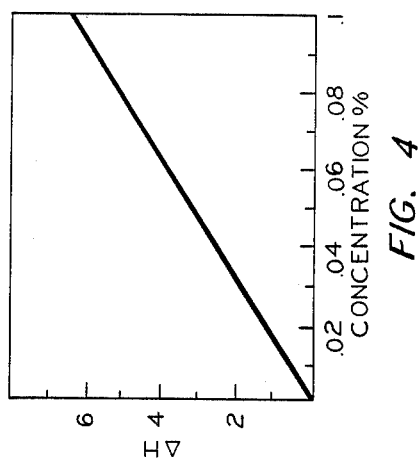
FIG. 4 illustrates a standard calibration curve for the apparatus of the present invention.
Figure 3:
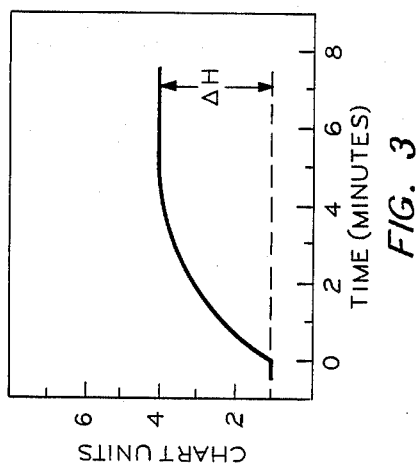
FIG. 3 is a graphical representation of the response of a strip chart recorder.

After preparing the enzyme probe and setting up equipment including a strip chart recorder, a suitable beaker with a stir bar, and a magnetic stirrer, the apparatus was calibrated by preparing a standard calibration curve as illustrated in FIG. 4. The curve of FIG. 4 was established by generating a series of response curves as illustrated in FIG. 3. Referring to FIG. 3 a baseline portion of the curve was established by immersing the enzyme sensor 80 in a volume of buffer solution as indicated in Table III, and setting the trace on the strip chart at a convenient location by adjusting potentiometer 44.

Starting with a high concentration standard solution, of 0.1 volume %, a volume as indicated in Table III was injected into the stirred beaker. Variable resistor 42 was adjusted for a convenient full scale trace on the strip chart recorder. The calibration was repeated for at least 3 calibration points covering the concentration range of 0.1–0.01%.

TABLE III

|  | Ethanol | Glucose | Lactose | Lactic Acid |
|---|---|---|---|---|
| Sample Volume, mL | 0.1 | 0.2 | 0.5 | 0.1 |
| Buffer Volume, mL | 3.9 | 3.8 | 3.5 | 3.9 |
| Detection limit, % (2 mL sample volume) | 0.0001 | 0.001 | 0.002 | 0.0005 |

For an unknown sample analysis retain the settings of potentiometer 44 and variable resistor 42 used for obtaining the standard curve and inject a volume of the unknown sample which gives an on scale reading on the strip chart recorder. However, the sum of the buffer volume and unknown sample volume must remain constant and equal to the volume used for the standard curve.

After obtaining an on-scale reading for the unknown sample the concentration was read from the standard curve. Finally the concentration of the analyte in the unknown sample was calculated according to the following equation:

$$\text{Analyte concentration} = \text{Conc. from std. curve} \times V_{std}/V_{unk}$$

Where $V_{std}$ and $V_{unk}$ are the sample volumes of the standard and unknown solutions, respectively.

The invention has been described in terms of a preferred embodiment as illustrated in FIGS. 1 through 4. As has been previously stated, many different configurations can be utilized and also many different electrical circuits can be utilized to condition the output current from the polargraphic cell oxygen detector. In addition variations which do not affect the operation of the oxygen detector are within the scope of the present invention.

That which is claimed is:

1. Apparatus for measuring the concentration of a substance in a solution wherein the concentration of the substance in solution can be directly correlated with the depletion of oxygen in an enzymatically catalyzed reaction of the substance, said apparatus comprising:
    (a) an enzyme sensor comprising:
        (i) an oxygen detector having two electrodes enclosed in a probe and having a sensitive area on the probe tip, said oxygen detector effectively producing a detector output current signal representative of the dissolved oxygen contacting said sensitive area;
        (ii) a layer of at least one oxidase enzyme held against said sensitive area on the probe tip, wherein said oxidase enzyme effectively catalyzing the reaction of the substance with oxygen;
(b) electronic signal conditioning circuitry connected to said oxygen detector comprising:
  (i) circuit means, having an input and an output, for converting a current signal to a voltage signal;
  (ii) means for conducting said detector output current signal to the input of said circuit means wherein said detector output current signal is converted to a detector voltage signal;
  (iii) means for establishing a first measurement signal at the output of said circuit means wherein said first measurement signal is representative of the concentration of dissolved oxygen contacting said sensitive area in the absence of the enzymatically catalyzed reaction of the substance with oxygen;
  (iv) means for establishing an offset correction current for said detector output current which nulls said first measurement signal; and
  (v) means for establishing a second measurement signal at the output of said circuit means wherein said second measurement signal is representative of the concentration of dissolved oxygen contacting said sensitive area in the presence of the enzymatically catalyzed reaction of the substance with oxygen and is thereby representative of the concentration of the substance in the solution.

2. Apparatus in accordance with claim 1 wherein said means for establishing an offset correction current for said detector output current which nulls said first measurement signal comprises:
  means for providing an external current to said input of said circuit means, wherein said external current is adjustable such that said first measurement signal can be nulled.

3. Apparatus in accordance with claim 1 additionally comprising:
  means for adjusting said voltage signal responsive to the actual temperature of said oxygen detector, and
  means for providing an essentially constant polarizing voltage across said oxygen detector.

4. Apparatus in accordance with claim 3 wherein said circuit means comprises an operational amplifier connected as a currentto-voltage converter and wherein the feedback signal for the operational amplifier is derived from a first resistive voltage divider connected between said output and ground.

5. Apparatus in accordance with claim 4 wherein said means for adjusting said voltage signal responsive to the actual temperature of said oxygen detector comprises a thermistor disposed for sensing the temperature of said oxygen detector wherein said thermistor is connected to said first resistive voltage divider.

6. Apparatus in accordance with claim 5 wherein said means for providing an external current to said input of said first circuit means comprises a second resistive voltage divider having a moveable contact connected to said input of said first circuit means, wherein said external current is provided to said input in parallel with said detector output current.

7. A method for obtaining an analysis of the concentration of a substance in a solution wherein the concentration of the substance can be directly correlated with the depletion of oxygen in an enzymatically catalyzed reaction of the substance and wherein an oxygen detector having two electrodes enclosed in a probe and having a layer of at least one oxidaze enzyme held against a sensitive area on the probe tip, generates a detector output current signal, and wherein electronic signal conditioning circuit means having an input and an output is connected to said oxygen detector and converts said detector output current signal to a voltage signal, said method comprising the steps of:
  establishing a first measurement signal at said output of said signal conditioning circuit means wherein said first measurement signal is representative of the concentration of dissolved oxygen contacting said sensitive area in the absence of a catalytic reaction of the substance with oxygen;
  establishing an offset correction current for said detector output current which nulls said first measurement signal; and
  establishing a second measurement signal at the output of said signal conditioning circuit means after nulling said first measurement signal wherein said second measurement signal is representative of the concentration of dissolved oxygen contacting said sensitive area in the presence of a catalytic reaction of the substance with oxygen and is thereby representative of the concentration of the substances in a solution.

8. A method in accordance with claim 7 wherein said step of establishing an offset correction current for said detector output current comprises:
  providing an external current to said input of said circuit means and adjusting said external current to null said first measurement signal.

9. A method in accordance with claim 8 wherein a thermistor is disposed for sensing the actual temperature of said oxygen detector additonally comprising the step of:
  adjusting said voltage signal responsive to the actual temperature of said oxygen detector.

* * * * *